United States Patent
Hunt et al.

(10) Patent No.: US 7,740,646 B2
(45) Date of Patent: *Jun. 22, 2010

(54) ADHESIVES FOR USE WITH SUTURE SYSTEM MINIMIZE TISSUE EROSION

(75) Inventors: John V. Hunt, Cincinnati, OH (US); Ronald J. Kolata, Cincinnati, OH (US); Mark S. Ortiz, Milford, OH (US); Frederick E. Shelton, Hillsboro, OH (US); Douglas J. Turner, Cincinnati, OH (US); James W. Voegele, Cincinnati, OH (US); Christopher W. Widenhouse, Clarkesville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/533,571

(22) Filed: Sep. 20, 2006

(65) Prior Publication Data

US 2007/0233188 A1 Oct. 4, 2007

Related U.S. Application Data

(63) Continuation-in-part of application No. 11/394,130, filed on Mar. 31, 2006, now abandoned.

(51) Int. Cl.
*A61B 17/04* (2006.01)
*A61B 17/06* (2006.01)

(52) U.S. Cl. ..................... 606/228; 606/222

(58) Field of Classification Search ......... 606/228–231, 606/222; 604/144
See application file for complete search history.

(56) References Cited

U.S. PATENT DOCUMENTS

| 3,459,188 | A | * | 8/1969 | Roberts | 604/29 |
| 4,159,720 | A | * | 7/1979 | Burton | 424/423 |
| 5,080,663 | A | | 1/1992 | Mills et al. | |

(Continued)

FOREIGN PATENT DOCUMENTS

EP 1545336 6/2005

(Continued)

OTHER PUBLICATIONS

U.S. Appl. No. 11/394,130.*

(Continued)

*Primary Examiner*—Julian W Woo
*Assistant Examiner*—Melissa Ryckman

(57) ABSTRACT

A design for a suture for use in suture appositioning techniques, and a method for use are disclosed. In one embodiment the suture may comprise a hollow length having a wall forming a lumen, which may serve as a conduit through which fluid may be pumped and discharged through a plurality of perforations in the wall. In another embodiment the suture may comprise a plurality of suture members connected by a connecting member. In one embodiment of a method disclosed, a suture having a hollow length having a wall forming a lumen, with a plurality of perforations in the wall, may be placed in a stitching procedure to apposition tissues, and a fluid such as an adhesive, adhesive activating agent or drug may be pumped through the lumen and discharged out the perforations for various beneficial effects.

12 Claims, 8 Drawing Sheets

U.S. PATENT DOCUMENTS

| | | | |
|---|---|---|---|
| 5,376,101 | A | 12/1994 | Green et al. |
| 5,437,681 | A | 8/1995 | Meade et al. |
| 5,462,558 | A | 10/1995 | Kolesa et al. |
| 5,514,159 | A | 5/1996 | Matula et al. |
| 5,540,705 | A | 7/1996 | Meade et al. |
| 5,569,197 | A * | 10/1996 | Helmus et al. ......... 604/102.02 |
| 5,571,119 | A | 11/1996 | Atala |
| 5,709,693 | A | 1/1998 | Taylor |
| 5,713,910 | A | 2/1998 | Gordon et al. |
| 5,752,939 | A * | 5/1998 | Makoto ...................... 604/175 |
| 5,814,071 | A | 9/1998 | McDevitt et al. |
| 5,855,559 | A * | 1/1999 | Van Tassel et al. .......... 600/486 |
| 6,036,694 | A | 3/2000 | Goble et al. |
| 6,197,014 | B1 * | 3/2001 | Samson et al. .............. 604/524 |
| 6,346,111 | B1 | 2/2002 | Gordon et al. |
| 6,443,962 | B1 | 9/2002 | Gaber |
| 6,454,778 | B2 | 9/2002 | Kortenbach |
| 6,494,888 | B1 | 12/2002 | Laufer et al. |
| 6,506,196 | B1 | 1/2003 | Laufer |
| 6,558,400 | B2 | 5/2003 | Deem et al. |
| 6,656,194 | B1 | 12/2003 | Gannoe et al. |
| 6,660,032 | B2 * | 12/2003 | Klumb et al. .............. 623/1.13 |
| 6,663,639 | B1 | 12/2003 | Laufer et al. |
| 6,719,763 | B2 | 4/2004 | Chung et al. |
| 6,719,764 | B1 | 4/2004 | Gellman et al. |
| 6,746,460 | B2 | 6/2004 | Gannoe et al. |
| 6,755,843 | B2 | 6/2004 | Chung et al. |
| 6,773,440 | B2 | 8/2004 | Gannoe et al. |
| 6,835,200 | B2 | 12/2004 | Laufer et al. |
| 6,908,427 | B2 | 6/2005 | Fleener et al. |
| 6,932,819 | B2 | 8/2005 | Meade et al. |
| 2002/0107530 | A1 | 8/2002 | Sauer et al. |
| 2003/0083674 | A1 | 5/2003 | Gibbens, III |
| 2003/0171760 | A1 | 9/2003 | Gambale |
| 2003/0181924 | A1 | 9/2003 | Yamamoto et al. |
| 2003/0233104 | A1 | 12/2003 | Gellman et al. |
| 2003/0233108 | A1 | 12/2003 | Gellman et al. |
| 2004/0034369 | A1 | 2/2004 | Sauer et al. |
| 2004/0044354 | A1 | 3/2004 | Gannoe et al. |
| 2004/0059350 | A1 | 3/2004 | Gordon et al. |
| 2004/0082963 | A1 | 4/2004 | Gannoe et al. |
| 2004/0088008 | A1 | 5/2004 | Gannoe et al. |
| 2004/0122473 | A1 | 6/2004 | Ewers et al. |
| 2004/0138682 | A1 | 7/2004 | Onuki et al. |
| 2004/0147941 | A1 | 7/2004 | Takemoto et al. |
| 2004/0147958 | A1 | 7/2004 | Lam et al. |
| 2004/0162568 | A1 | 8/2004 | Saadat et al. |
| 2004/0194790 | A1 | 10/2004 | Laufer et al. |
| 2004/0210243 | A1 | 10/2004 | Gannoe et al. |
| 2004/0260344 | A1 | 12/2004 | Lyons et al. |
| 2005/0015101 | A1 | 1/2005 | Gibbens, III et al. |
| 2005/0055038 | A1 | 3/2005 | Kelleher et al. |
| 2005/0070931 | A1 | 3/2005 | Li et al. |
| 2005/0075653 | A1 | 4/2005 | Saadat et al. |
| 2005/0125034 | A1 | 6/2005 | Cichocki |
| 2005/0125035 | A1 * | 6/2005 | Cichocki .................... 606/222 |
| 2007/0032800 | A1 * | 2/2007 | Ortiz et al. .................. 606/148 |

FOREIGN PATENT DOCUMENTS

| | | |
|---|---|---|
| EP | 1569709 | 9/2005 |
| FR | 2747908 | 10/1997 |
| WO | WO00/61012 | 10/2000 |
| WO | WO01/10312 | 2/2001 |
| WO | WO01/66001 | 9/2001 |
| WO | WO02/35980 | 5/2002 |

OTHER PUBLICATIONS

EPO Search Report for Application No. 07251426.8, dated Aug. 27, 2007.

* cited by examiner

ADHESIVES FOR USE WITH SUTURE SYSTEM MINIMIZE TISSUE EROSION

RELATED APPLICATIONS

This application is a continuation-in-part of U.S. patent application Ser. No. 11/394,130 filed on Mar. 31, 2006, and entitled ENDOSCOPIC SUTURING DEVICE, which is incorporated by reference in its entirety for any and all purposes. This application claims the benefit of said earlier application to the extent permissible.

FIELD OF THE INVENTION

The present invention relates generally to methods and devices used to apposition tissues by suturing. More particularly, the present invention relates to devices and methods of suturing tissues using special sutures of unconventional designs that provide for greater distribution of tissue holding force, thereby reducing the concentration of stress and the likelihood of tissue erosion proximate to sutures, and provide for introduction of various fluids along suture passages to provide various benefits and advantages.

BACKGROUND OF THE INVENTION

Suture-based tissue appositioning techniques are relatively simple and have been in use for many years. Applications have included rejoining previously connected tissues separated by traumatic events. Applications also have included joining previously unconnected tissues as part of therapeutic procedures. For example, in procedures relating to bypassing or truncating organs forming body lumens, or removing diseased organs connecting body lumens, such as, for example, an intestinal resection or bypass or a prostatectomy, it is necessary to join previously unconnected tissues forming body lumens to restore/maintain bodily functions. More recently, suture-based applications have included joining tissues, such as, for example, portions of the stomach wall, in connection with bariatric stomach volume reduction surgery.

In any suture-based apposition of tissues, forces necessary to hold the joined tissues together cause concentration of stresses in the tissues about the sutures and their passages through the tissues. The magnitude and concentration of these stresses will be affected by the size of the suture material used, the number/frequency of stitches placed, the tension introduced into the sutures during the suturing procedure, the strength, resilience and firmness of the joined tissues, and the stresses placed on the tissues and the tissue connection as a result of patient movement and/or bodily function and activity following the suturing procedure. Depending upon one or more of these factors, concentrated stresses in the tissues surrounding the sutures may be conducive to erosion or tearing of the tissues about the sutures, loosening of the tissue connection, and even separation of the joined tissues. For example, when a patient eats following bariatric stomach volume reduction surgery, the reduced active portions of the stomach walls, or reduced stomach pouch, containing the food consumed, may be subjected to increased stress, increasing the stress concentrated in the stomach wall tissues proximate to the sutures. This may cause the tissues surrounding the sutures to erode or tear, possibly resulting in loosening of the stomach wall connection or even separation of the joined stomach wall tissues over a period of time, unacceptably reducing the amount of time the stomach volume reduction exists to provide the intended benefits for the patient.

Therefore, it would be desirable to have a suturing method and/or device that reduce the likelihood of tissue erosion and separation of the joined tissues, and enhance the effectiveness and benefits of the suturing procedure.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF EMBODIMENTS OF THE INVENTION

Figure 1:
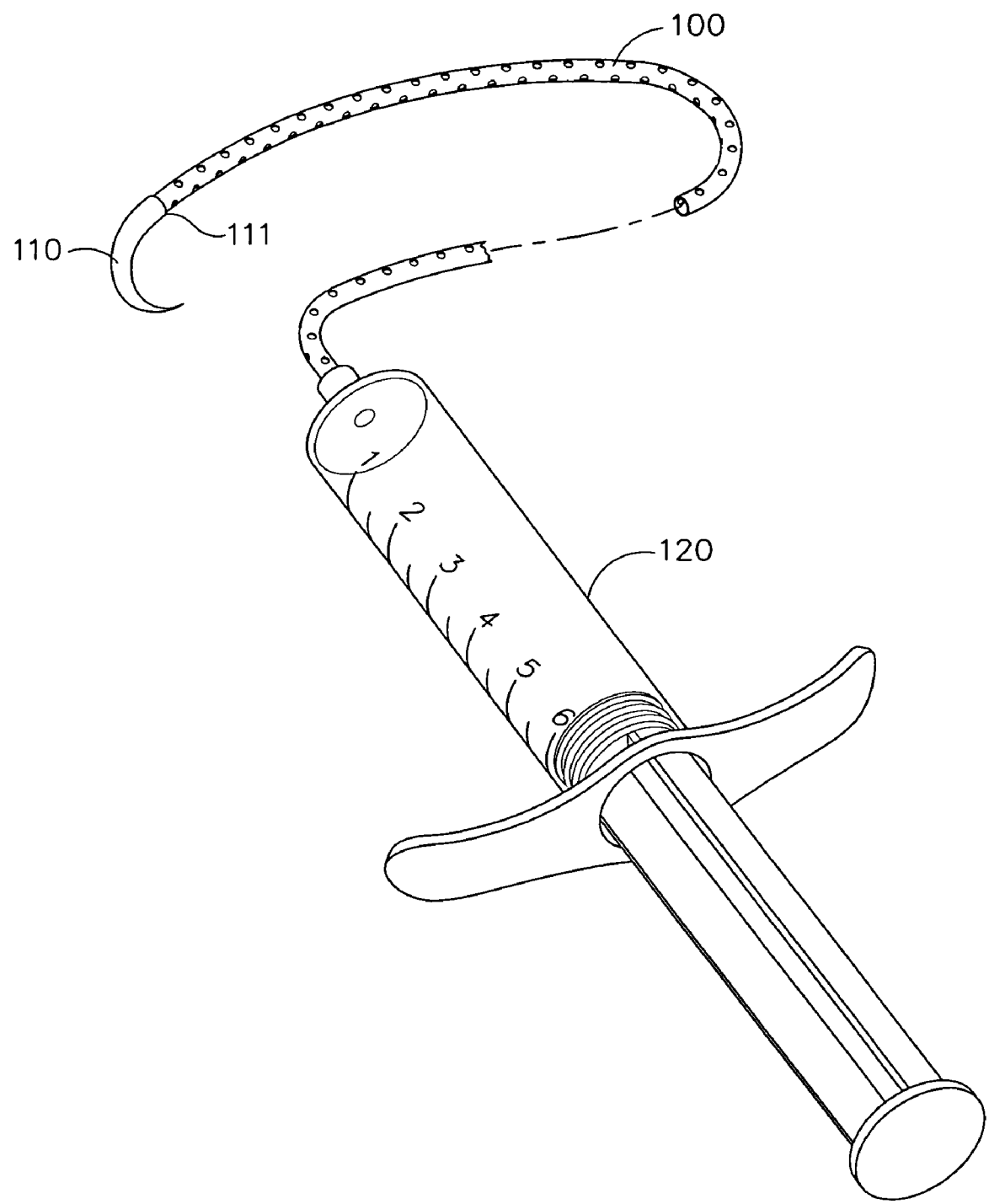
FIG. 1 is a perspective view of one possible embodiment of a suture within the scope of the present invention shown connected to a syringe and a suturing needle.
Figure 2:
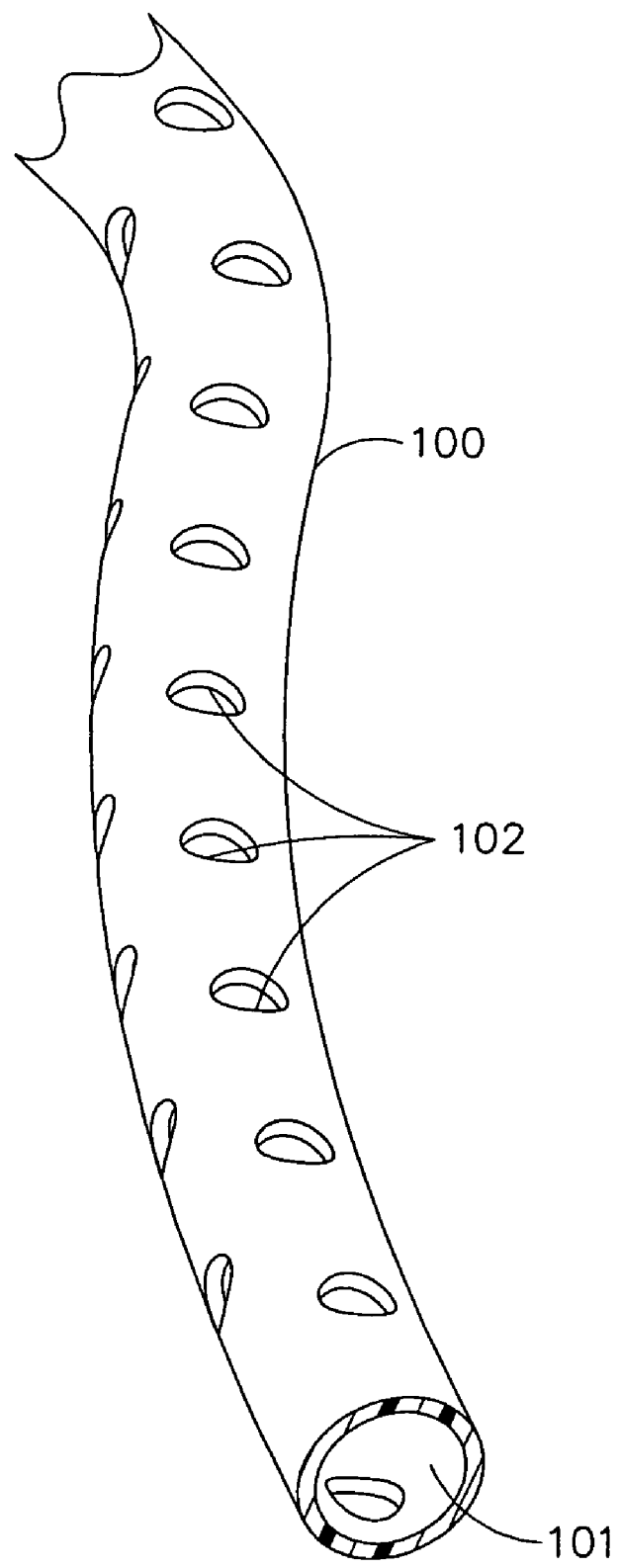
FIG. 2 is an expanded perspective view of a portion of the suture shown in FIG. 1.
Figure 8:
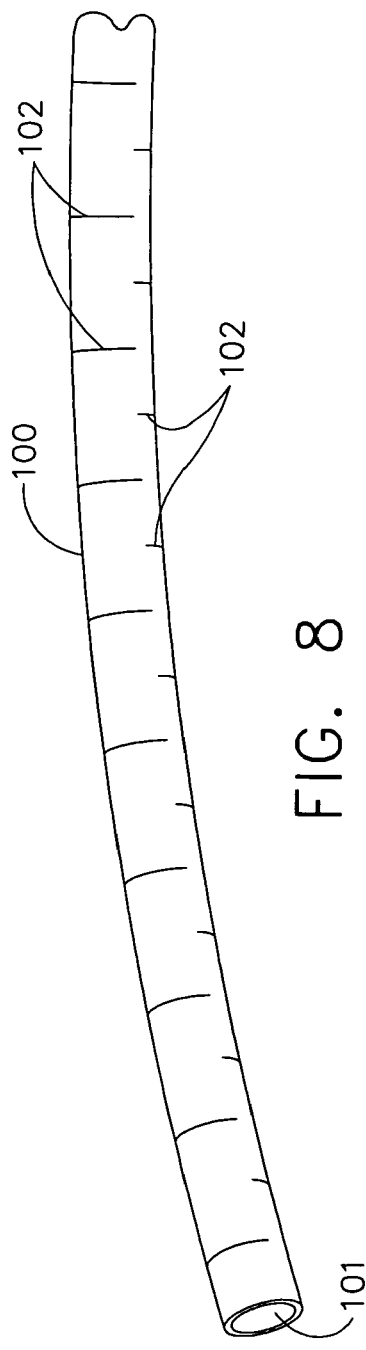
FIG. 8 is a perspective view of a portion of another possible embodiment of a suture within the scope of the present invention.
Figure 9:
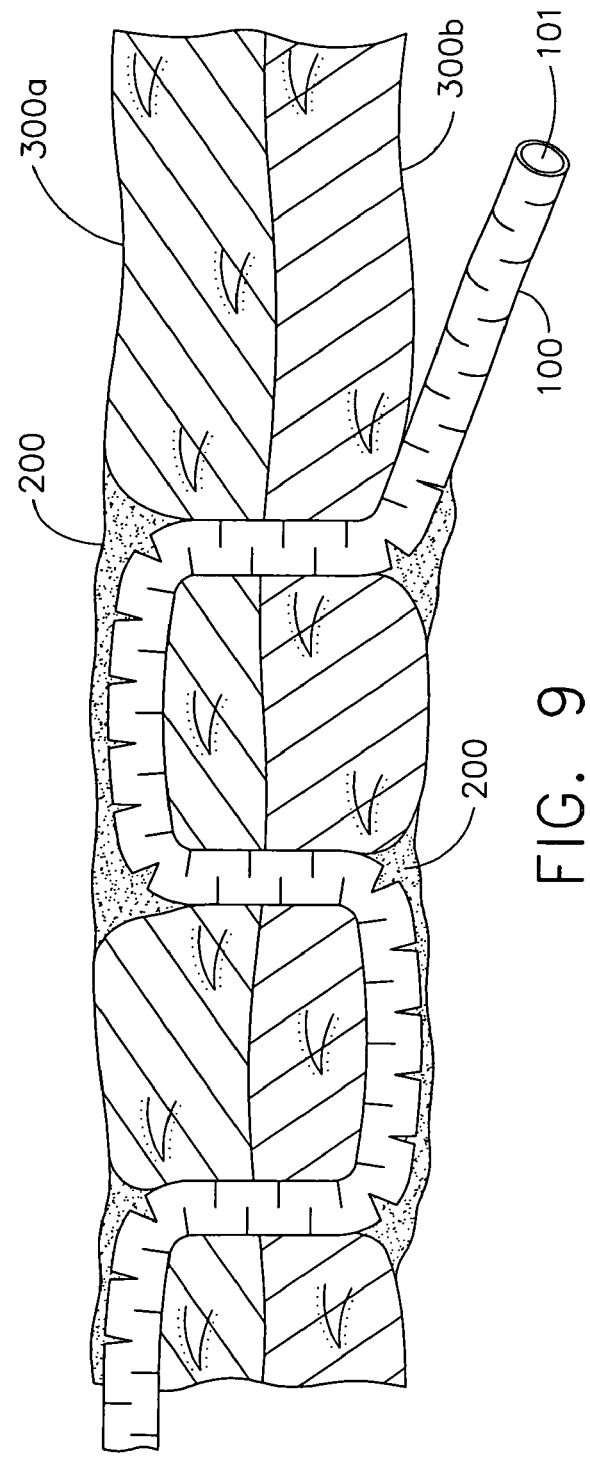
FIG. 9 is a perspective illustration of suture of the type shown in FIG. 8, shown as it might be placed to hold two tissue layers together by one possible suturing technique, following pumping of fluid into the suture.

Turning to the Drawings, wherein like numerals refer to like components throughout the several views, FIG. 1 is a perspective view of a possible embodiment of a suture 100 within the scope of the present invention, shown connected to a syringe 120 and a suturing needle 110 via, for example, a swaged connection 111. FIG. 2 is an expanded perspective view of a portion of the suture 100 shown in FIG. 1. It can be seen that suture 100 has a length that is hollow, having a wall forming a lumen 101. Suture 100 may be larger in cross sectional area than a conventional solid suture that would typically be used in the particular procedure. Suture 100 also may have perforations 102 along all or a portion of its length. As may be appreciated from FIGS. 2 and 8, perforations 102 may be circular holes or simply cuts or slashes perforating the wall of suture 100 along all or a portion of its length. Alternatively, perforations 102 may have any other size, shape, pattern, orientation and frequency along the length of suture 100 suitable to a balance between serving the purposes of retaining the tensile strength desired for suture 100, and providing for the desired characteristics of conduction, flow and discharge of fluid through lumen 101 and out perforations 102 as will be described below. For example, perforations 102 may be arranged in a continuous or interrupted pattern; in varying patterns; in a radial or spiral pattern; or in one or more longitudinal/linear or non-linear rows along the length of suture 100.

Figure 3:
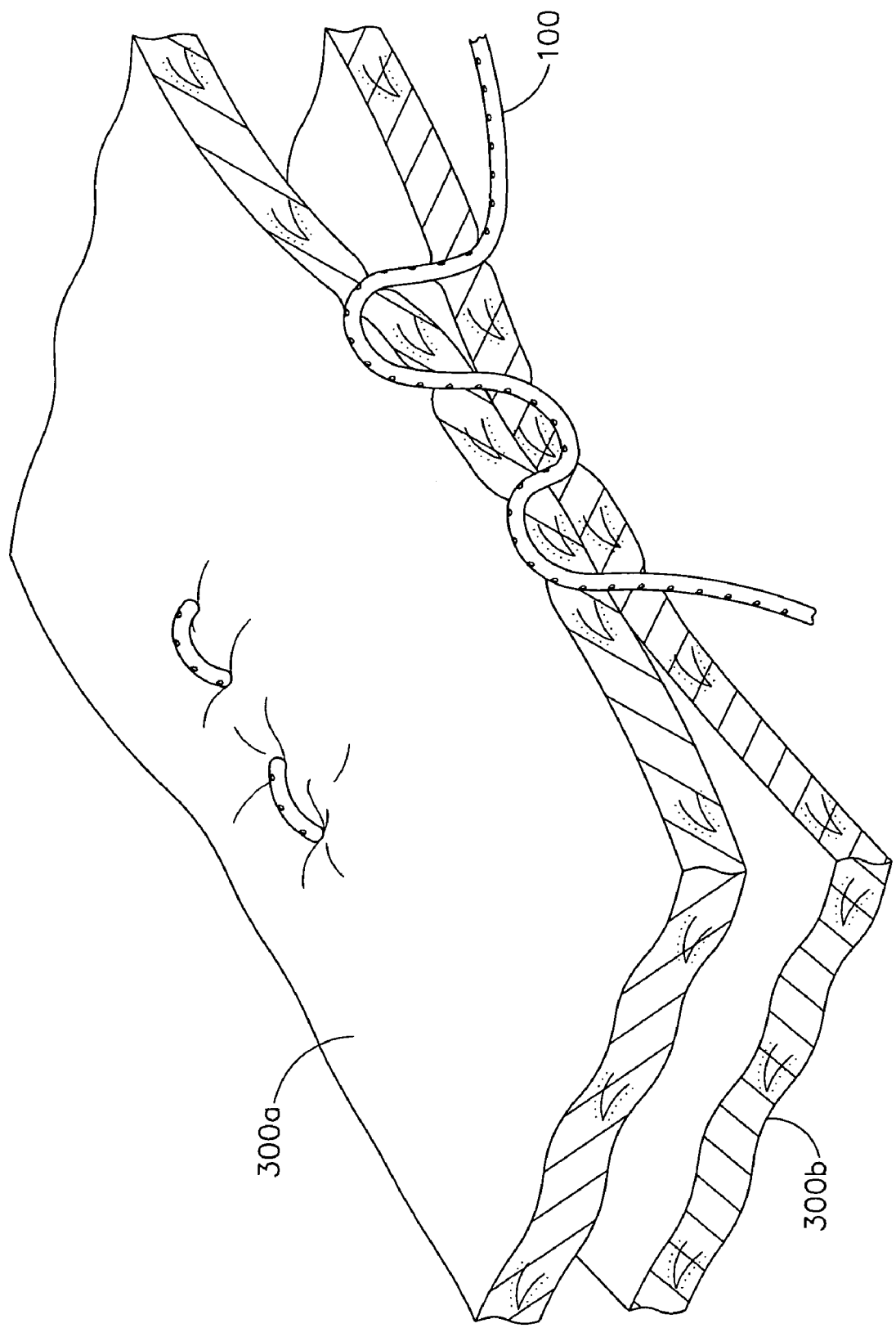
FIG. 3 is a perspective illustration of suture of the type shown in FIG. 1, shown as it might be placed to hold two tissue layers together by one possible suturing technique.

FIG. 3 illustrates a possible method by which suture 100 may be placed in a suturing procedure to join or connect a first tissue layer 300*a* and a second tissue layer 300*b* in a desired location. An instrument such as needle 110 (see FIG. 1) may be used by a surgeon to pierce the tissues and create a passage through them and draw suture 100 therebehind and through the tissues along the passage. It will be appreciated that if suture 100 is hollow, it will have a larger surface area per unit of length than a solid suture of the same material and linear material density. Thus, the force applied by suture 100 upon the tissue layers 300*a* and 300*b* when the suture 100 is drawn tight will be spread over larger surface areas of the tissues as compared with similar placement of conventional solid suture material, reducing the concentration of stresses in the tissues surrounding the installed suture 100.

Figure 4:
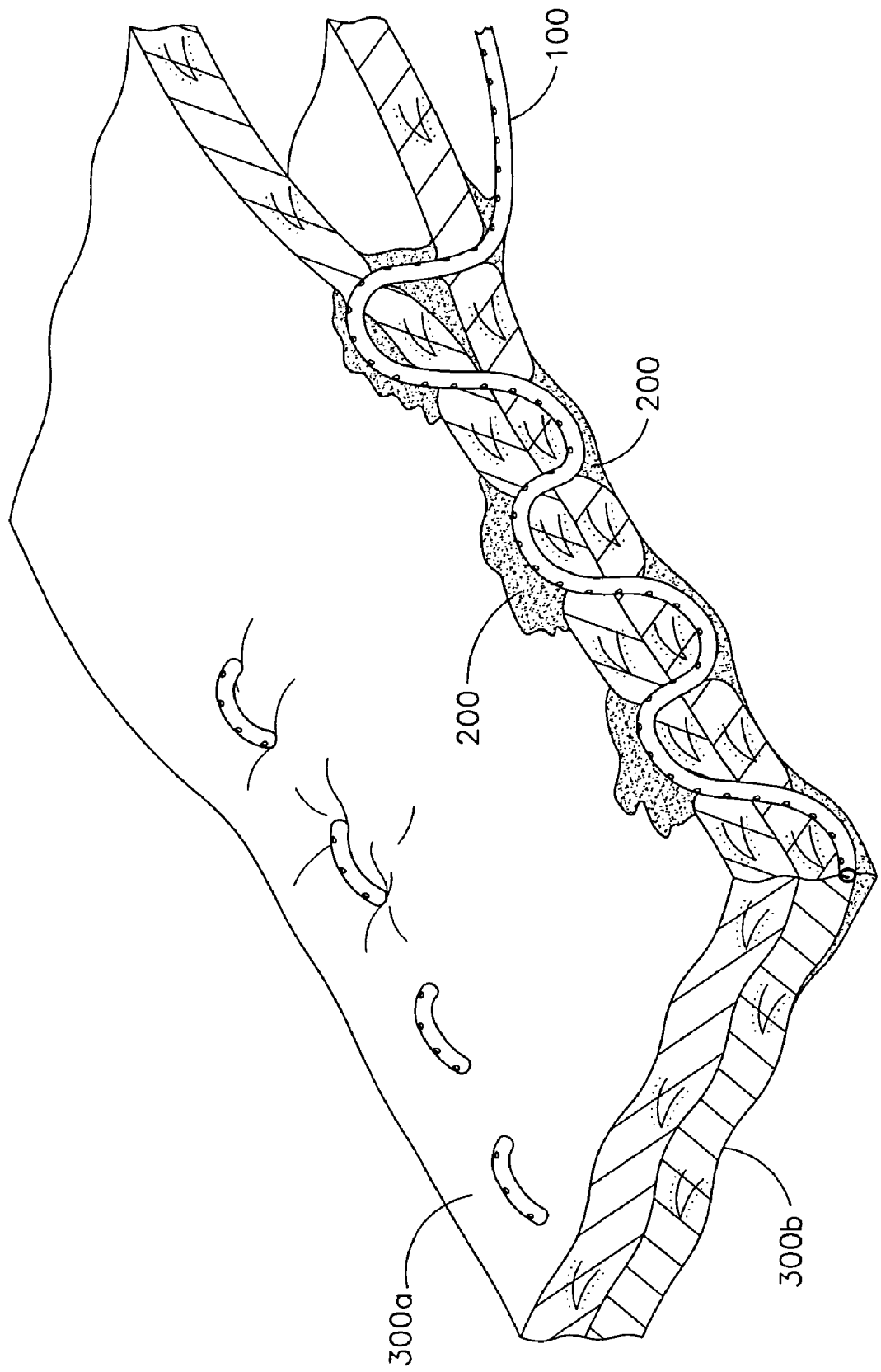
FIG. 4 is a perspective illustration of suture of the type shown in FIG. 1, shown as it might be placed to hold two tissue layers together by one possible suturing technique, following pumping of fluid through the suture.

Referring to FIG. 4, it can be appreciated that if suture 100 has perforations 102, for example, as depicted in FIG. 2, a fluid 200 may be injected or pumped through lumen 101 of suture 100, and will flow therethrough and be discharged out through perforations 102 into the tissues surrounding the installed suture 100. The fluid may be, for example, a fluid adhesive or sealant. Suitable fluid adhesives or sealants may include, for example, cyanoacrylate or isocyanate adhesives. As may be appreciated from FIG. 1, fluid may be pumped into suture 100 by use of a syringe 120, or any other suitable fluid pumping or injection device. Referring again to FIG. 4, and also FIG. 8, when a fluid 200 comprising a suitable adhesive or sealant is thereby pumped through lumen 101 of suture 100 and discharged outside suture 100 through perforations 102, it will form deposits of adhesive proximate to suture 100 as shown, which will adhere to both the tissues 300*a*, 300*b* and the suture 100, and subsequently cure. After curing, the deposits of adhesive may serve to distribute holding force over greater portions and surface areas of the tissue, reducing concentrations of stress in the joined tissues proximate to the suture 100, and thus reducing the likelihood of tissue erosion or tearing about or proximate to the sutures.

Figure 5:
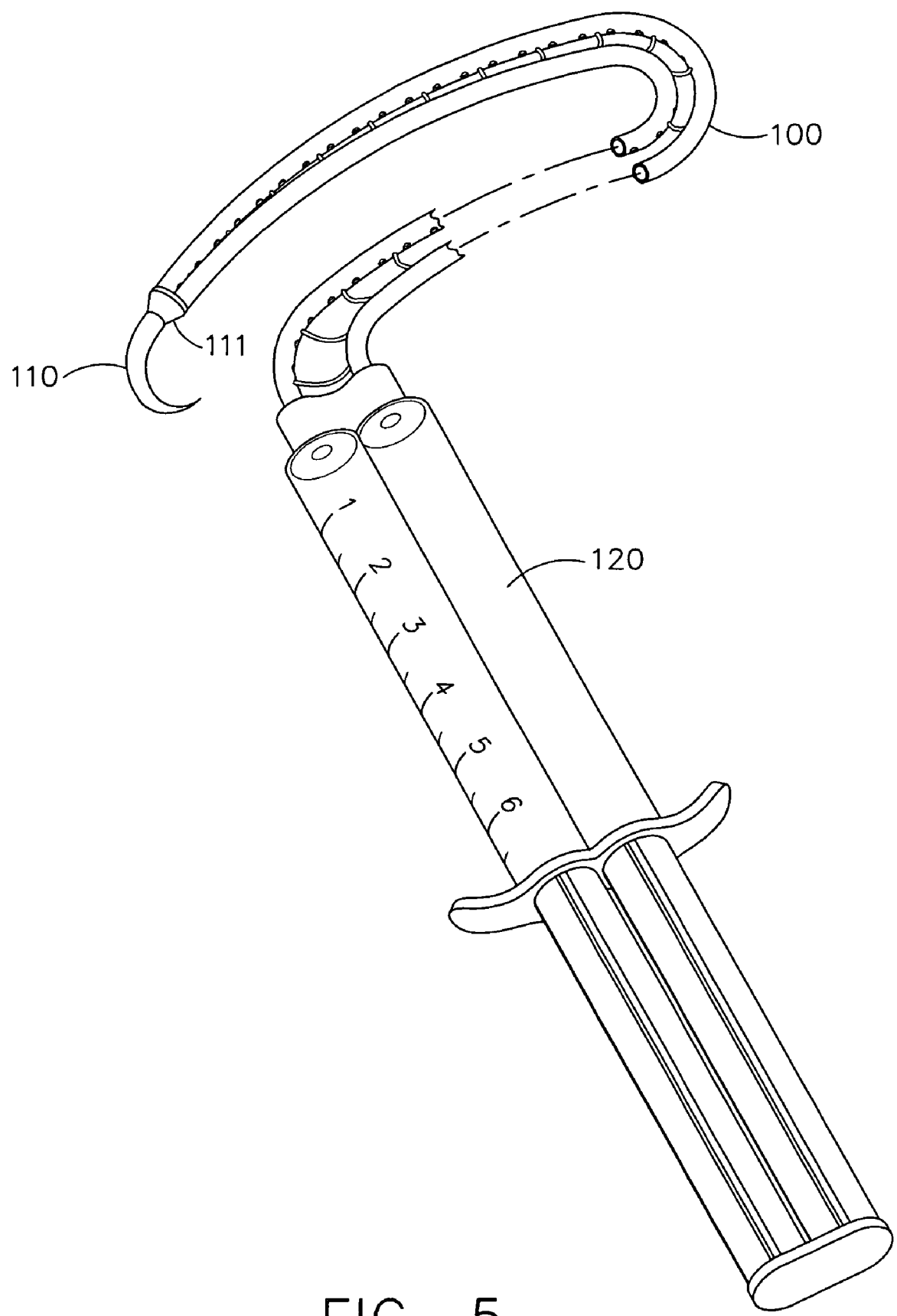
FIG. 5 is a perspective view of another possible embodiment of a suture within the scope of the present invention shown connected to a syringe and a suturing needle.
Figure 6:
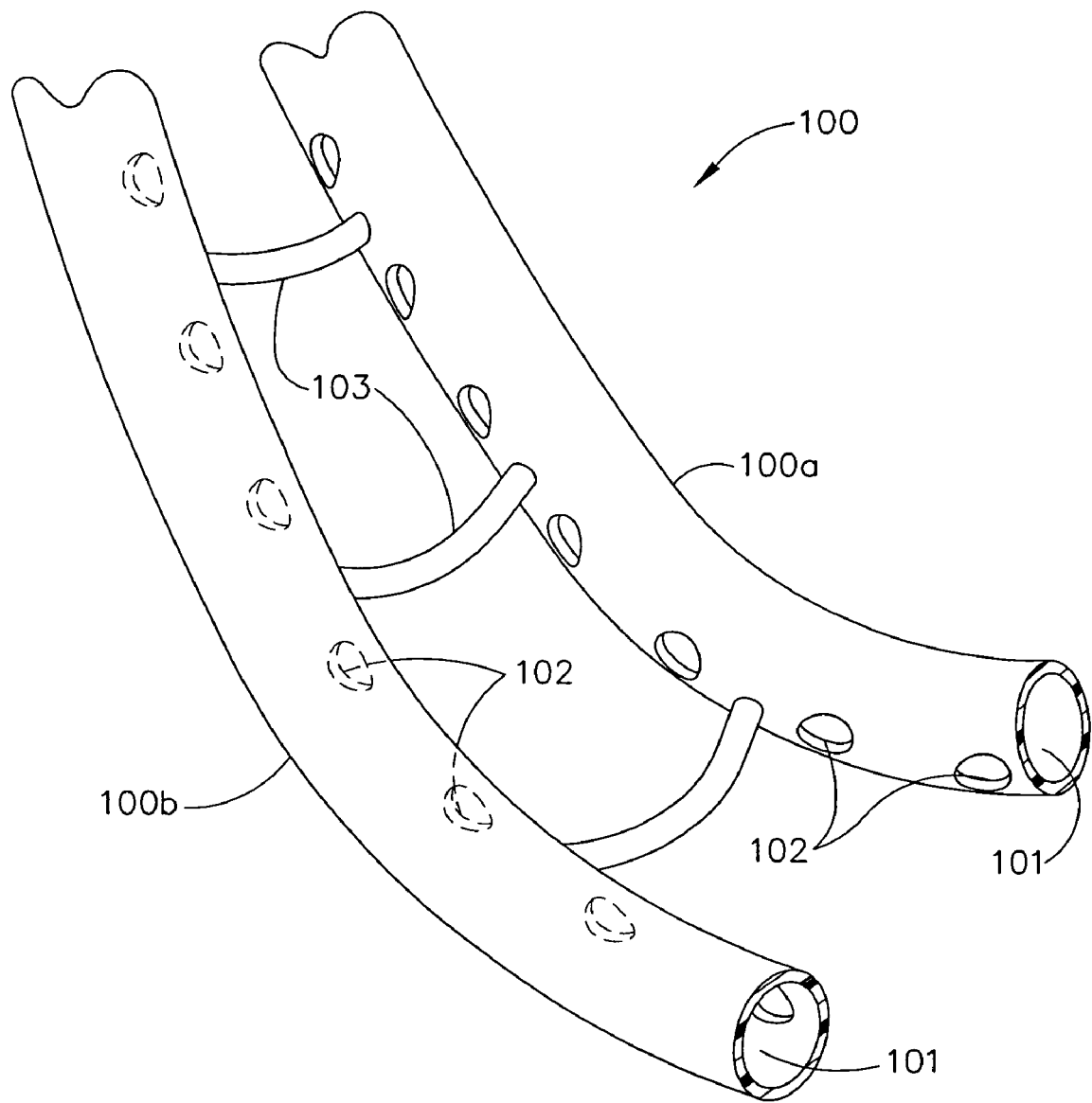
FIG. 6 is an expanded perspective view of a portion of the suture shown in FIG. 5.

FIG. 5 depicts another possible embodiment of a suture 100 within the scope of the present invention, shown connected to a syringe 120 and a suturing needle 110 via a swaged connection 111. FIG. 6 is an expanded perspective view of a portion of the suture 100 shown in FIG. 1. It can be seen that suture 100 may include a plurality, or in the depicted embodiment, first and second, suture members 100*a* and 100*b*, either or both of which may have a hollow length, having a wall forming a lumen. Suture members 100*a* and/or 100*b* also may have perforations 102 along all or a portion of their hollow lengths. As may be appreciated from FIGS. 6 and 8, perforations 102 may be circular holes or simply cuts or slashes perforating the walls of suture members 100*a*, 100*b* along all or a portion of their lengths. Alternatively, perforations 102 may have any other size, shape, orientation and frequency along the lengths of suture members 100*a*, 100*b* suitable to a balance between serving the purposes of retaining the tensile strength needed for suture 100, and providing for the desired conduction, flow and discharge of fluid through lumens 101 and out perforations 102 as described above. In the possible embodiment depicted in FIG. 6, suture members 100*a* and 100*b* are connected by a series of connecting members 103. Connecting members 103 may be formed of a flexible, elastic or springy material, such as for example, a suitable plastic, such that they may flex in response to application of forces urging suture members 100*a* and 100*b* together, and return to an extended position upon cessation of such forces, thus acting to urge suture members 100*a* and 100*b* toward a spaced-apart relationship.

Figure 7:
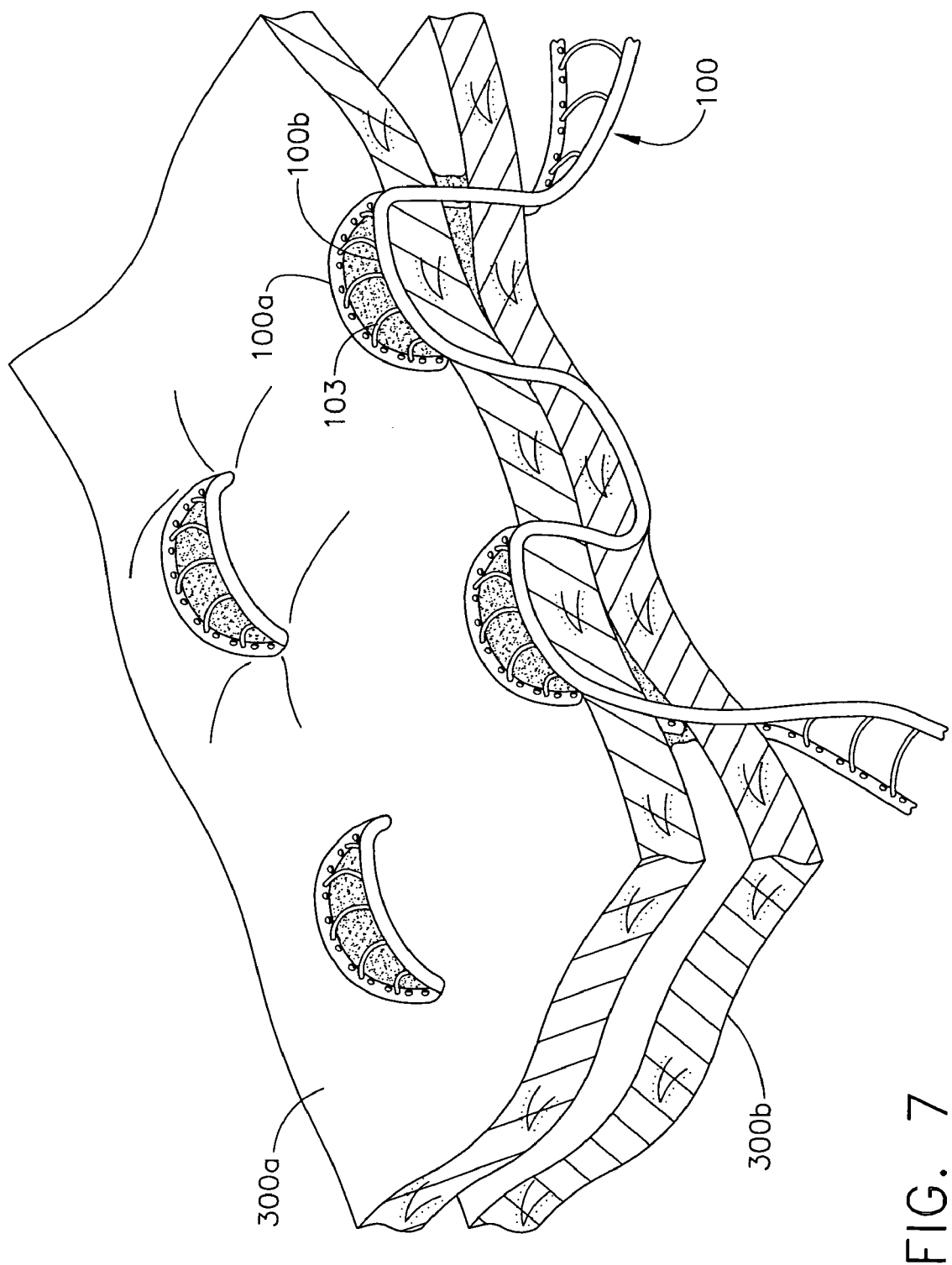
FIG. 7 is a perspective illustration of suture of the type shown in FIG. 5, shown as it might be placed to hold two tissue layers together by one possible suturing technique.

FIG. 7 illustrates a possible method by which suture 100 as shown in FIG. 6 may be placed in a suturing procedure to join or connect a first tissue layer 300*a* and a second tissue layer 300*b* in a desired location. An instrument such as needle 110 (see FIG. 5) may be used by a surgeon to pierce the tissues and create a passage through them, and draw suture 100 therebehind and through the tissues along the passage. It will be appreciated that if there are a plurality of suture members 100*a* and 100*b*, when drawn tight they will distribute tissue holding force over a larger tissue surface area per unit of length than a comparable placement of a conventional single suture that would otherwise be used. Thus, the force applied by suture 100 upon the tissue layers 300*a* and 300*b* when the suture 100 is drawn tight will be spread over larger surface areas of the tissues, reducing the concentration of stresses in the tissues surrounding the installed suture 100. It also will be appreciated that as suture 100 is drawn through a single passage in the tissues created by needle 110, suture members 100*a* and 100*b* will be urged together by the tissues as they pass therethrough along the passage. Connecting members 103 flex and thereby allow suture members 100*a* and 100*b* to be urged together. When suture 100 is not restrained by tissues surrounding a passage therethrough, however, connecting members 103 are permitted to extend and urge suture members 100*a* and 100*b* to a spaced-apart relationship, as shown in FIG. 7. With suture members 100*a* and 100*b* in this spaced-apart relationship, the tissue holding force applied by suture 100 upon the tissue layers 300*a* and 300*b* when the suture 100 is drawn tight will be even more effectively distributed over larger surface areas of the tissues through suture members 100*a*, 100*b* and connecting members 103, further reducing the concentration of stresses in the tissues surrounding the suture 100.

If one or more of the plurality of suture members 100*a*, 100*b* have a hollow length with a lumen 101 and perforations 102, in the manner discussed above, the plural-member suture 100 shown in FIG. 7 may have fluid pumped through one or more lumens 101 thereof by, for example, syringe 120 (see FIG. 5) or any other suitable pumping device. It will be appreciated that if the fluid comprises an adhesive or sealant, holding force distributing effects similar to those described above can be realized. It will be appreciated also that connecting members 103 also may be in contact and be subject to bonding with the discharged adhesive or sealant, and may serve to channel, control, compartmentalize and/or contain deposits of adhesive or sealant and thereby serve to improve or control their location and uniformity, as well as promote or improve formation of a band- or strap-like structure, upon curing of the adhesive or sealant, that may have enhanced holding force distributing capabilities.

It will be appreciated that connecting members 103 may have any suitable form, including rod-like members situated approximately perpendicular to suture members 100*a*, 100*b* as shown in FIG. 6, any other suitable discrete connecting members of any suitable shape and in any suitable orientation, or alternatively, a connecting member may consist of webbing, mesh, or any other flexible connecting structure, and even a structure through which fluids may flow to/from suture members 100*a* and 100*b*.

It will be appreciated that, as an alternative to or in addition to serving as a conduit for fluid comprising adhesive or sealant to distribute tissue holding forces, hollow suture 100 and/or suture members 100*a* and 100*b*, for example, having a plurality of perforations 102, may serve as conduits and dispersal mechanisms for the injection of fluids comprising other substances, such as lubricants, adhesive activation agents, or drugs such as antibiotics, pain-reducing agents, tissue sclerosing agents or other drugs. It also will be appreciated that hollow suture 100 and/or suture members 100a and 100b may have fluid pumped into their lumens prior to or during placement within tissues in a suturing procedure, for various purposes including, for example, lubrication of suture surfaces to ease suture passage through tissues, evacuation of air from within the suture lumen(s) or improved transport to and dispersal of fluid within the appositioned tissues. Additionally, sutures 100 and/or suture members 100a and 100b may be coated for desired effects with substances such as, for example, a lubricant, a hydrophilic coating, an adhesive activation or curing agent, or drugs such as, for example, a tissue sclerosing agent and/or an antibiotic.

From the foregoing it will be appreciated that various combinations of one or more non-conventional suture members may be formed and placed to provide suture-based tissue appositions that distribute tissue holding forces over larger areas than conventional solid suture techniques allow, thus, reducing the likelihood of tissue erosion and separation following the procedure. It also will be appreciated that the use of one or a plurality of hollow and suitably perforated suture members in a suturing procedure provides a means for transport and distribution of fluids along the suture passage for various beneficial effects. Thus, it will be appreciated that the embodiments disclosed and described herein are only examples of a greater number of possible embodiments of methods and devices that may be formed and utilized to attain the benefits and advantages described herein. Accordingly, the scope of the invention is limited only by the claims appended hereto, and equivalents thereof.

We claim:

1. A device for use in appositioning of tissues, comprising in combination:
    a first suture having a hollow length, said first suture comprising a distal end and a proximal end, wherein said first suture comprises a single non-rigid tubular structure of unitary construction, the hollow length having a wall forming a lumen, wherein the wall provides an outer surface having at least one perforation therethrough, wherein the outer surface extends continuously along the hollow length of the first suture, wherein said outer surface is configured for direct contact with said tissues, wherein said perforations are configured to provide direct fluid communication between said tissues and said lumen;
    said first suture further comprising a suturing needle attached to the distal end of said first suture, wherein the needle is configured to penetrate tissue and create a passage therethrough;
    a curable fluid tissue adhesive deliverable directly to the tissues through said lumen via said perforation and in contact with said first suture, wherein, upon delivery to said tissues, said adhesive adheres to said tissues and said first suture such that the adhesive is configured to distribute a holding force to tissue adjacent to the first suture by adhering the tissue;
    an adhesive delivery apparatus in fluid communication with the first suture, wherein the adhesive delivery apparatus contains a first portion of the adhesive, wherein the first suture contains a second portion of the adhesive, wherein the adhesive delivery apparatus is operable to urge the second portion of the adhesive through the first suture and out of the at least one perforation of the first suture to dispense the second portion of the adhesive to adjacent tissue;
    wherein said first suture has sufficient flexibility to be drawn behind said needle through said passage in said tissue; and
    a second suture connected to the first suture by a flexible connecting member, wherein the connecting member comprises a first end and a second end, wherein the connecting member terminates at the first end at the first suture, wherein the connecting member terminates at the second end at the second suture, wherein the connecting member is configured to flex in response to application of an inward force urging the first suture and the second suture together, wherein the connecting member is configured to urge the first suture and the second suture toward a spaced-apart relationship upon cessation of the inward force.

2. The device of claim 1 wherein said adhesive comprises a cyanoacrylate.

3. The device of claim 1 wherein said adhesive comprises an isocyanate.

4. The device of claim 1 further comprising a drug delivered through said lumen.

5. The device of claim 4 wherein the drug comprises an antibiotic.

6. The device of claim 4 wherein the drug comprises a tissue sclerosing agent.

7. The device of claim 1 further comprising a fluid adhesive activating agent delivered through said lumen and in contact with said fluid tissue adhesive.

8. The device of claim 1 further comprising a pump fluidly connected to the lumen.

9. The device of claim 8 wherein the pump comprises a syringe.

10. The device of claim 1 wherein the second suture has a hollow length, the hollow length having a wall forming a lumen, the wall having at least one perforation therethrough.

11. The device of claim 1 further comprising a lubricant coating on said first suture.

12. The device of claim 1 further comprising an inner surface on said wall, and an adhesive activating agent coating on at least one of said inner and outer surfaces.

* * * * *